United States Patent [19]

Weyer et al.

[11] 4,182,775
[45] Jan. 8, 1980

[54] BENZOIC ACIDS AND PROCESS FOR THEIR PREPARATION

[75] Inventors: Rudi Weyer, Kelkheim; Volker Hitzel, Hofheim am Taunus; Ernold Granzer, Kelkheim, all of Fed. Rep. of Germany

[73] Assignee: Hoechst Aktiengesellschaft, Frankfurt, Fed. Rep. of Germany

[21] Appl. No.: 829,876

[22] Filed: Sep. 1, 1977

[30] Foreign Application Priority Data

Sep. 4, 1976 [DE] Fed. Rep. of Germany ....... 2639935

[51] Int. Cl.$^2$ .................. C07C 101/42; A01N 9/20
[52] U.S. Cl. ........................... 424/319; 424/309; 424/275; 562/442; 562/451; 560/37; 560/42; 549/64; 549/72
[58] Field of Search ............. 260/518 R, 518 A, 519; 560/442, 451; 562/37, 41; 424/309, 319

[56] References Cited

U.S. PATENT DOCUMENTS

| 3,150,170 | 9/1964 | Cavallini et al. ............ 260/518 R |
| 3,725,417 | 4/1973 | Holland .............................. 560/37 |
| 3,870,715 | 3/1975 | Hansl ........................... 260/518 R |
| 4,136,197 | 1/1979 | Hubner et al. ................... 562/451 |
| 4,151,303 | 4/1979 | Witte et al. ....................... 562/451 |

FOREIGN PATENT DOCUMENTS 2500157   7/1976   Fed. Rep. of Germany ...... 260/518 R Primary Examiner—James H. Reamer
Attorney, Agent, or Firm—Curtis, Morris & Safford

[57] ABSTRACT

Benzoic acids of the general formula I

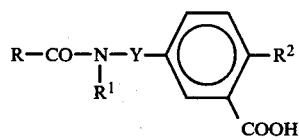

in which R, $R^1$, $R^2$ and Y have the meanings as mentioned in the following, and which in the form of the free compounds or in the form of the physiologically tolerated salts and esters possess valuable pharmacological properties, processes for preparing them, pharmaceutical preparations containing them, and their use as or in medicaments.

9 Claims, No Drawings

BENZOIC ACIDS AND PROCESS FOR THEIR PREPARATION

The present invention relates to benzoic acids and to a process for preparing them.

The present invention provides benzoic acids of the general formula I

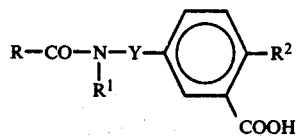

which in the form of the free compounds or in the form of the physiologically tolerated salts and esters possesses valuable pharmacological properties.

In the general formula, R represents
(a) a phenyl radical which may be mono-, di- or trisubstituted by alkyl having 1 to 3 carbon atoms, alkoxy having 1 to 4 carbon atoms, alkenoxy having 3 to 4 carbon atoms, $CF_3$ or halogen,
(b) a phenyl radical which may be mono- or disubstituted by halogen, alkyl or alkoxy having 1 to 4 carbon atoms each and which is linked with CO via Z, Z being a methylene group which may be substituted by halogen, alkoxy having 1 to 4 carbon atoms, or a vinyl group or
(c) a thiophene radical which may be mono- or disubstituted by alkyl having 1 to 3 carbon atoms, alkoxy having 1 to 4 carbon atoms, or halogen, $R^1$ is hydrogen or alkyl having up to 4 carbon atoms,
Y is a saturated hydrocarbon radical having 1 to 3 carbon atoms,
$R^2$ is hydrogen, alkyl having 1 to 4 carbon atoms, or halogen.

If R is substituted, the substituents may be identical or different.

Among the substituents of R, alkyl and alkoxy represent preferably methyl and methoxy, and halogen is preferably chlorine. $CF_3$ appears but once as the substituent for the phenyl radical. R has preferably the meanings mentioned under (a) and (b). Preference is given particularly to compounds, in which the phenyl group has been substituted by chlorine.

If the meaning of $R^1$ is alkyl, preference is given to methyl. Hydrogen is mentioned in particular for $R^1$.

For $R^2$ preference is given to methyl and chlorine, methyl being particularly preferred.

Y represents preferably the $-CH_2-CH_2-$group.

Besides the benzoic acids of the formula I and the physiologically tolerated salts and esters thereof, the present invention also provides processes for the preparation of these compounds, pharmaceutical preparations containing the same or consisting of them and their use as or in (a) pharmaceutical composition(s).

The processes for preparing the compounds of the invention comprise
(a) reacting an amine of the general formula II

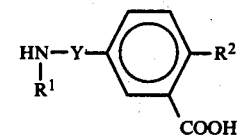

or the salt or ester thereof with a reactive derivative of the acid

RCOOH, (b) converting in a compound of the general formula III

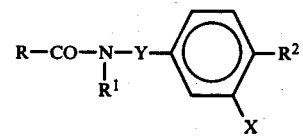

in which X represents a radical convertible into a carboxyl group, said radical into the carboxyl group,
(c) for preparing compounds of the general formula I, in which the radical R contains an alkoxy group, alkylating the corresponding hydroxy compound, and converting the compounds obtained optionally into free benzoic acids or the esters or salts thereof.

For the preparation according to process (a) there may be used as reactive derivatives of the acid RCOOH acid halides, anhydrides, mixed anhydrides, esters and azides. Preference is given to acid chlorides and mixed anhydrides. The compounds of formula II may be used as free acids, as esters or salts, the salts being not only salts of the carboxyl group with bases but also those of the amines with acids. The reaction may be carried out in an aqueous, hydrous or anhydrous solution and in the presence of inorganic or organic bases.

According to process (b) the radical X may be converted in known manner into a carboxyl group, either by hydrolysis or by oxidation. As radicals which can be converted hydrolytically into a carboxyl group there are to be mentioned preferably the nitrile group, the amide group and the iminoether group, the iminoether group possibly also being converted directly into the ester group. By way of oxidation, for example, the hydroxymethyl, aminomethyl, formyl and acyl groups may be converted into carboxyl groups, i.e. by the action of oxidizing agents, preferably permanganate, chromate or hypochlorite, or else, silver oxide or atmospheric oxygen.

For the preparation according to process (c) the hydroxy compounds are reacted in known manner with alkylating agents, such as alkyl halide or dialkyl sulfate.

The compounds of the invention may be converted into physiologically tolerated salts. Salts of this kind are alkali metal salts, alkaline earth metal salts or salts with appropriate amines. The preparation of these salts is effected in known manner, for example by reaction with the free bases or carbonates.

The benzoic acids may also be converted into esters according to known processes. Compounds that are suitable for esterification are in principle all alcohols. However, use is preferably made of lower alcohols, such as methanol, ethanol, propanol, and also glycol, ethanolamine or glycol ether.

The compounds of the invention have valuable therapeutical properties and are distinguished by a lipid lowering action.

Various benzoic acids having a lipid lowering and hypoglycaemic action have already been described in literature (for example, phenoxyalkyl-benzoic acids and phenylalkoxybenzoic acids, cf. German Offenlegungsschrift No. 24 39 458). However, it was surprising that the novel acylaminoalkylbenzoic acids of the invention also show a pronounced lipid lowering action.

The lipid lowering action can be determined in various test models. In the standard test, male rats having a normal serum lipid content are given the preparation orally for 8 days in a dosage of 100 mg/kg by means of the esophageal sound.

Blood is withdrawn before and after the treatment, and the concentration of cholesterol in the serum is determined according to the method of Lauber and Richterich, and the triglycerides are determined according to the method of Eggstein and Kreutz. The values obtained are compared with the starting concentrations and also with a control group.

A part of the compounds also shows a hypoglycaemic action.

The hypoglycaemic action of the compounds of the invention can for example be evaluated, besides the lipid lowering action, in the test model described before, by determining before and after the treatment the blood sugar concentration according to the method of Hagedorn-Jensen in the autoanalyzer or according to the hexokinase method. However, it may also be evaluated by administering the preparations in doses of 100 mg/kg to normally fed rabbits and determining the blood sugar over a longer period of time according to one of the above-mentioned methods.

The compounds of the invention are preferably used for the preparation of compositions to be administered orally and having a lipid lowering action for the treatment of lipidosis and/or diabetes mellitus; they may be applied as such or in the form of their salts or esters, or in the presence of substances causing the salt formation.

The novel compounds may be applied either as such or in admixture with pharmacologically suitable carriers, an oral form of application being preferred.

As pharmaceutical compositions there are mentioned preferably tablets which contain, besides the products of the invention, the common carriers and auxiliary agents, such as talc, starch, lactose, tragacanth or magnesium stearate.

A preparation containing the compounds described as active ingredients, for example, a tablet or a powder with or without additives, is suitably brought into an appropriate dosage unit form. There is to be chosen a dose which is adapted to the effectiveness of the active substance used and to the desired effect. The dosage unit is suitably in the range of from about 0.1 to 2 g, preferably from 0.5 to 1 g, however, use may also be made of higher or lower dosage units which are optionally to be divided or multiplied prior to their application.

The benzoic acids of the invention may be used by themselves or in combination with other agents. As substances which are suitable for a combination of this kind there may be mentioned: Circulatory preparations in the broadest sense, however above all agents dilating the coronary vessels, such as chromonar or prenylamin, and antihypertensive agents, such as reserpine, α-methyl-dopa or clonidine, other antihyperlipidemic agents or geriatric agents; psychopharmacological agents, such as chlorodiazepoxide, diazepame or meprobamate, as well as vitamins. For the treatment of diabetes mellitus there may be mentioned not only hypoglycaemic sulfonyl ureas as further active ingredients, but also compounds of a different chemical structure, for example, biguanides, especially phenylethyl biguanide or dimethyl biguanide.

The following Examples serve to illustrate the invention by showing some of the numerous process variants which may be used for the synthesis of the compounds of the invention. However, they are not to represent any restriction of the subject of the invention.

EXAMPLE 1

5-(3-Chloro-benzamido-methyl)-2-methyl-benzoic acid

30 Milliliters of 2N-sodium hydroxide solution are added to 4 g of 5-(aminomethyl)-2-methyl-benzoic acid x HCl (melting point 232° to 240° C. (decomp.), prepared by reacting 5-(chloromethyl)-2-methyl-benzoic acid with hexamethylene-tetramine and separating the reaction product with hydrochloric acid) in 30 ml of acetone.

Then 3.5 g of 3-chlorobenzoyl chloride in a small amount of acetone are added dropwise, while stirring and cooling with ice, the mixture is stirred for further 2 hours at room temperature, the precipitated substance is dissolved with diluted ammonia, is filtered while adding charcoal, and the filtrate is acidified. The precipitated 5-(3-chloro-benzamido-methyl)-2-methyl-benzoic acid is dissolved and recrystallized from diluted methanol and melts at a temperature in the range of from 207° to 209° C.

In an analogous manner there is obtained:
5-(4-chloro-benzamido-methyl)-2-methyl-benzoic acid, melting point 205° to 207° C. (from diluted methanol),
5-(5-chloro-2-methoxy-benzamido-methyl)-2-methyl-benzoic acid, melting point 183° to 185° C. (from diluted methanol), and
5-(2,5-dichloro-benzamido-methyl)-2-methyl-benzoic acid, melting point 215° to 217° C. (from diluted methanol).

EXAMPLE 2

5-(2-[4-Chloro-benzamido]-ethyl)-2-methyl-benzoic acid (a) 5-(2-Amino-ethyl)-2-methyl-benzoic acid:

34.6 Grams of 5-cyanomethyl-2-methyl-benzoic acid (melting point 158° to 160° C., prepared from 5-chloromethyl-2-methyl-benzoic acid and potassium cyanide) are hydrogenated in 700 ml of methanol in the presence of 300 ml of 10% sodium hydroxide solution and Raney nickel at 70° C. and 100 atmospheres gage of hydrogen. After cooling, the methanol is distilled off, the residue is acidified with concentrated hydrochloric acid and evaporated. The residue is boiled out with methanol, the methanolic solution is evaporated, the hydrochloride obtained is treated with acetone. Melting point 264° to 266° C. (decomp.).

(b) 5-(2-[4-Chloro-benzamido]-ethyl)-2-methyl-benzoic acid

13 Grams of 5-(2-aminoethyl)-2-methyl-benzoic acid x HCl are dissolved in 70 ml of acetone and 90 ml of 2N-sodium hydroxide solution. 10.5 Grams of 4-chlorobenzoyl chloride in 20 ml of acetone are added dropwise, while stirring and cooling with ice, then the mixture is continued to be stirred for 2 hours at room temperature, the acetone is removed under reduced pressure, the residue is reprecipitated from diluted ammonia and recrystallized from diluted methanol.

The 5-(2-[4-chloro-benzamido]-ethyl)-2-methyl-benzoic acid obtained melts at a temperature in the range of from 216° to 218° C.

In an analogous manner, the following compounds are obtained:

5-(2-<3-Chloro-benzamido>-ethyl)-2-methyl-benzoic acid, m.p. 178° to 180° C. (from diluted methanol);

5-(2-<4-methyl-benzamido>-ethyl)-2-methyl-benzoic acid, m.p. 211° to 213° C. (from diluted methanol);

5-(2-<4-methoxy-benzamido>-ethyl)-2-methyl-benzoic acid, m.p. 212° to 213° C. (from diluted methanol);

5-(2-<2-methoxy-benzamido>-ethyl)-2-methyl-benzoic acid, m.p. 158° to 160° C. (from diluted methanol);

5-(2-<4-bromo-benzamido>-ethyl)-2-methyl-benzoic acid, m.p. 231° to 233° C. (from diluted methanol);

5-(2-<5-chloro-2-methoxy-benzamido>-ethyl)-2-methyl-benzoic acid, m.p. 150° to 152° (from diluted methanol);

5-(2-<4-chloro-2-methoxy-benzamido>-ethyl)-2-methyl-benzoic acid, m.p. 152° to 154° (from diluted methanol);

5-(2-<5-chloro-2-ethoxy-benzamido>-ethyl)-2-methyl-benzoic acid, m.p. 144° to 146° (from diluted methanol);

5-(2-<4-chloro-2-ethoxy-benzamido>-ethyl)-2-methyl-benzoic acid, m.p. 136° to 138° C. (from diluted methanol);

5-(2-<4-chloro-2-n-propoxy-benzamido>-ethyl)-2-methyl-benzoic acid, m.p. 133° to 135° (from diluted methanol);

5-(2-<5-chloro-2-n-butoxy-benzamido>-ethyl)-2-methyl-benzoic acid, m.p. 137° to 139° (from diluted methanol);

5-(2-<4-chloro-2-n-butoxy-benzamido>-ethyl)-2-methyl-benzoic acid, m.p. 130° to 132° C. (from diluted methanol);

5-(2-<2-allyloxy-5-chloro-benzamido>-ethyl)-2-methyl-benzoic acid, m.p. 114° to 115° (from diluted methanol);

5-(2-<5-methyl-2-methoxy-benzamido>-ethyl)-2-methyl-benzoic acid, m.p. 127° to 129° (from diluted methanol);

5-(2-<4-chloro-2-methyl-benzamido>-ethyl)-2-methyl-benzoic acid, m.p. 184° to 186° (from diluted methanol);

5-(2-<3-chloro-4-methyl-benzamido>-ethyl)-2-methyl-benzoic acid, m.p. 194° to 196° C. (from diluted methanol);

5-(2-<3,4-dichloro-benzamido>-ethyl)-2-methyl-benzoic acid, m.p. 205° to 207° (from diluted methanol);

5-(2-<3,5-dichloro-benzamido>-ethyl)-2-methyl-benzoic acid, m.p. 222° to 224° (from diluted methanol);

5-(2-<2,4,5-trimethoxy-benzamido>-ethyl)-2-methyl-benzoic acid, m.p. 220° to 222° C. (from ethanol);

5-(2-<2,5-dichloro-benzamido>-ethyl)-2-methyl-benzoic acid, m.p. 222° to 224° C. (from methanol/dioxan);

5-(2-<2,4-dichloro-benzamido>-ethyl)-2-methyl-benzoic acid, m.p. 183° to 185° C. (from diluted methanol);

5-(2-<3-methyl-benzamido>-ethyl)-2-methyl-benzoic acid, m.p. 185° to 187° C. (from diluted methanol);

5-(2-<2-chloro-5-methyl-benzamido>-ethyl)-2-methyl-benzoic acid, m.p. 204° to 206° C. (from diluted methanol);

2-methyl-5-(2-<3-trifluoromethyl-benzamido>-ethyl)-benzoic acid, m.p. 163° to 165° C. (from diluted methanol);

2-methyl-5-(2-<4-trifluoromethyl-benzamido>-ethyl)-benzoic acid, m.p. 201° to 202° C. (from diluted methanol);

5-(2-<2,4-dimethyl-benzamido>-ethyl)-2-methyl-benzoic acid, m.p. 193° to 195° C. (from diluted ethanol);

5-(2-<5-chloro-thiophene-2-carboxamido>-ethyl)-2-methyl-benzoic acid, m.p. 175° to 177° C. (from diluted methanol);

5-(2-<3,5-dichloro-2-methoxy-benzamido>-ethyl)-2-methyl-benzoic acid, m.p. 116° to 118° C. (from ethanol);

5-2-<2,4,5-trichloro-benzamido>-ethyl)-2-methyl-benzoic acid, m.p. 224° to 226° C. (from ethanol);

5-(2-<4-fluoro-benzamido>-ethyl)-2-methyl-benzoic acid, m.p. 175° to 177° C. (from diluted ethanol);

5-(2-<3-fluoro-benzamido>-ethyl)-2-methyl-benzoic acid, m.p. 205° to 207° C. (from diluted methanol);

5-(2-<1-methoxy-1-phenyl-acetamido>-ethyl)-2-methyl-benzoic acid, m.p. 126° to 127° C. (from diluted methanol);

5-(2-<(4-chlorophenyl)-methoxy-acetamido>-ethyl)2-methyl-benzoic acid, m.p. 142° to 143° C. (from diluted methanol);

5-(2-cinnamoylamino-ethyl)-2-methyl-benzoic acid, m.p. 213° to 215° C. (from isopropanol);

5-(2-<4-chloro-cinnamoylamino>-ethyl)-2-methyl-benzoic acid, m.p. 217° to 219° C. (from methanol);

5-(2-<2,4-dichloro-cinnamoylamino>-ethyl)-2-methyl-benzoic acid, m.p. 209° to 211° C. (from diluted methanol);

5-(2-phenoxyacetamido-ethyl)-2-methyl-benzoic acid, m.p. 144° to 146° C. (from diluted methanol);

5-(2-<4-chloro-phenoxyacetamido>-ethyl)-2-methyl-benzoic acid, m.p. 176° to 178° C. (from diluted methanol).

EXAMPLE 3

2-Chloro-5-(2-[5-chloro-2-methoxy-benzamido]-ethyl)-benzoic acid 2.5 Grams of 2-chloro-5-(2-aminoethyl)-benzoic acid×HCL (melt. point 264° to 268° C., prepared by the bromination of 2-chloro-5-methyl-benzoic acid, reaction of the bromide with potassium cyanide to give the nitrile, m.p. 140° to 143° C., and catalytic hydrogenation of the nitrile to give the amine) are mixed with the solution of 0.8 g of sodium hydroxide in 30 ml of water, then 2.1 g of 5-chloro-2-methoxy-benzoyl chloride in 30 ml of acetone are added dropwise to the mixture, while stirring and cooling, subsequently the mixture is continued to be stirred for 1 hour at room temperature, is acidified with diluted hydrochloric acid, then it is suction-filtered, the precipitate is reprecipitated from diluted ammonia and recrystallized from diluted methanol. The 2-chloro-5-(2-[5-chloro-2-methoxy-benzamido]-ethyl)-benzoic acid obtained melts at a temperature in the range of from 172° to 174° C.

In an analogous manner, the following products are obtained:

2-Chloro-5-(2-<2-ethoxy-5-chloro-benzamido>-ethyl)-benzoic acid, m.p. 147° to 150° (from diluted methanol);

2-chloro-5-(2-<2-n-butoxy-5-chloro-benzamido>-ethyl)-benzoic acid, m.p. 154° to 157° (from diluted methanol);

2-chloro-5-(2-<2-allyloxy-5-chloro-benzamido>-ethyl)-benzoic acid, m.p. 145° to 147° (from diluted methanol);

2-chloro-5-(2-<2-methoxy-benzamido>-ethyl)-benzoic acid, m.p. 148° to 150° (from diluted methanol);

2-chloro-5-(2-<4-chloro-benzamido>-ethyl)-benzoic acid, m.p. 150° to 152° (from diluted methanol).

EXAMPLE 4

2-Chloro-5-(4-chloro-benzamidomethyl)-benzoic acid 4.4 Grams of 2-chloro-5-(aminomethyl)-benzoic acid ×HCl (m.p. 220° to 230° C. (decomp.), prepared by reacting 5-bromomethyl-2-chloro-benzoic acid with hexamethylene-tetramine and splitting off the reaction product with hydrochloric acid) in 40 ml of acetone are mixed with the solution of 1.7 g of sodium hydroxide in 20 ml of water. The mixed anhydride prepared from 3.2 g of 4-chloro-benzoic acid, 2.5 g of triethylamine, and 2.3 g of chloroformic acid-methylester in 50 ml of acetone is added dropwise, while stirring and cooling, and the whole is continued to be stirred for 2 hours at room temperature.

Subsequently the acetone is removed under reduced pressure, the residue is mixed with diluted hydrochloric acid, is filtered off with suction, and the product obtained is dissolved and recrystallized from diluted methanol. The 2-chloro-5-(4-chloro-benzamidomethyl)-benzoic acid obtained melts at a temperature in the range of from 195° to 197° C.

In an analogous manner, 2-chloro-5-(5-chloro-2-methoxybenzamidomethyl)-benzoic acid is obtained, which has a m.p. in the range of from 196° to 197° C. (from dil. methanol).

EXAMPLE 5

3-(2-[4-Chloro-benzamido]-ethyl)-benzoic acid 4.1 Grams of 3-(2-amino-ethyl)-benzoic acid ×HCL (prepared by the bromination of 3-methyl-benzoic acid, reaction of the bromide, m.p. 147° to 149° C., with potassium cyanide to give the nitrile, m.p. 175° to 178° C., and hydrogenation of the nitrile to give the amine) in 30 ml of acetone are mixed with 30 ml of 2N-sodium hydroxide solution. 3.5 Grams of 4-chloro-benzoyl chloride in 20 ml of acetone are added dropwise to the mixture, while stirring and cooling, said mixture is then continued to be stirred for 2 hours at room temperature, the acetone is distilled off for the most part under reduced pressure, the residue is acidified, is filtered off with suction and recrystallized from diluted methanol. The 3-(2-[4-chloro-benzamido]-ethyl)-benzoic acid obtained melts at a temperature in the range of from 205° to 208° C.

EXAMPLE 6

5-(2-[4-Chloro-benzamido]-ethyl)-2-methyl-benzoic acid-ethyl-ester

6 Grams of 5-(2-[4-chloro-benzamido]-ethyl)-2-methyl-benzoic acid in 50 ml of ethanol are boiled for 4 hours with 1.5 ml of concentrated sulfuric acid at the reflux condenser. Subsequently the alcohol is distilled off for the most part, the residue is mixed with ice, the precipitate is filtered off with suction, is treated with diluted ammonia in order to remove the acid still present and is recrystallized from diluted ethanol. The 5-(2-[4-chloro-benzamido]-ethyl)-2-methyl-benzoic acid-ethylester obtained melts at a temperature in the range of from 116° to 118° C.

EXAMPLE 7

5-(2-[4-Chloro-benzamido]-1-methyl-ethyl)-2-methyl-benzoic acid 6.7 Grams of 5-(2-amino-1-methyl-ethyl)-1-methyl-benzoic acid in the form of the hydrochloride (m.p. 236° to 238° C., obtained by reaction of the 5-cyanomethyl-2-methyl-benzoic acid-methylester with diethylcarbonate and sodium alcoholate, methylation of the compound obtained with methyl iodide, separation of the carbethoxy group and hydrogenation of the nitrile) are dissolved with 45 ml of 2N-sodium hydroxide solution and 40 ml of acetone and are reacted with 5.3 g of 4-chloro-benzoyl chloride in a small amount of acetone, while stirring and cooling with ice. The mixture is continued to be stirred for 2 hours at room temperature, the acetone is removed under reduced pressure, and the residue is acidified. The precipitated acid is filtered off with suction, is reprecipitated from ammonia and recrystallized from methanol. The 5-(2-[4-chloro-benzamido]-1-methyl-ethyl)-2-methyl-benzoic acid obtained melts at a temperature of from 188° to 189° C.

We claim:

1. Benzoic acids of the general formula I

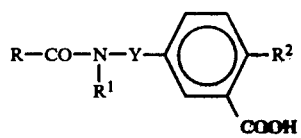

in which
R represents
(a) a phenyl radical which may be mono-, di- or trisubstituted by alkyl having 1 to 3 carbon atoms, alkoxy having 1 to 4 carbon atoms, alkenoxy having 3 to 4 carbon atoms, $CF_3$ or halogen,
(b) a phenyl radical which may be mono- or disubstituted by halogen, alkyl or alkoxy having 1 to 4 carbon atoms each and which is linked with CO via Z, Z being a methylene group which may be substituted by halogen, alkoxy having 1 to 4 carbon atoms or a vinyl group or,
(c) a thiophene radical which may be mono- or disubstituted by alkyl having 1 to 3 carbon atoms, alkoxy hving 1 to 4 carbon atoms, or halogen,
$R^1$ is hydrogen or alkyl having up to 4 carbon atoms,
Y is a saturated hydrocarbon radical having 1 to 3 carbon atoms, $R^2$ is alkyl having 1 to 4 carbon atoms, or halogen, as well as the physiologically tolerable salts and esters thereof.

2. A benzoic acid of the general formula

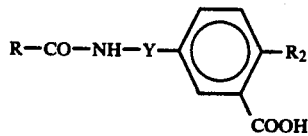

wherein
R is phenyl which may be substituted one to three times by alkyl of 1 to 3 carbon atoms, alkoxy of 1 to 4 carbon atoms, $CF_3$ or halogen, Y is alkylene of 1 to 3 carbon atoms, $R_2$ is methyl or chlorine, and the physiologically tolerable salts and esters thereof.

3. The compound 5-(2-[4-chloro-benzamido]-ethyl-2-methyl benzoic acid and the physiologically tolerable salts and esters thereof.

4. An oral lipid-lowering composition containing as its essential active component an effective amount of the compound defined in claim 1.

5. An oral lipid-lowering composition containing as its essential active component an effective amount of the compound defined in claim 2.

6. An oral lipid-lowering composition containing as its essential active ingredient an effective amount of a compound as defined in claim 3.

7. A method of treating a patient having hypolipidemia which comprises orally administering to the patient a lipid-lowering amount of the compound of claim 1.

8. A method of treating a patient having hypolipidemia which comprises orally administering to the patient a lipid-lowering amount of the compound of claim 2.

9. A method of treating a patient having hypolipidemia which comprises orally administering to the patient a lipid-lowering amount of the compound of claim 3.

* * * * *